(12) United States Patent
Beausoleil et al.

(10) Patent No.: US 7,233,711 B1
(45) Date of Patent: Jun. 19, 2007

(54) AUTONOMOUS EVANESCENT OPTICAL NANOSENSOR

(75) Inventors: Raymond G. Beausoleil, Redmond, WA (US); Philip J. Kuekes, Menlo Park, CA (US); R. Stanley Williams, Redwood City, CA (US)

(73) Assignee: Hewlett Packard Development Company, L.P., Houston, TX (US)

( * ) Notice: Subject to any disclaimer, the term of this patent is extended or adjusted under 35 U.S.C. 154(b) by 92 days.

(21) Appl. No.: 11/127,542

(22) Filed: May 11, 2005

(51) Int. Cl.
*G02B 6/00* (2006.01)
*G02B 6/12* (2006.01)
(52) U.S. Cl. .............................. 385/12; 385/14; 385/30
(58) Field of Classification Search ...................... None
See application file for complete search history.

(56) References Cited

U.S. PATENT DOCUMENTS

| 5,778,114 | A * | 7/1998 | Eslambolchi et al. ......... 385/12 |
| 7,106,448 | B1 * | 9/2006 | Vawter et al. .............. 356/461 |
| 2006/0045809 | A1 * | 3/2006 | Shirai et al. ............. 422/82.11 |
| 2006/0062508 | A1 * | 3/2006 | Guo et al. ..................... 385/12 |
| 2006/0147147 | A1 * | 7/2006 | Zourob et al. ................ 385/12 |

FOREIGN PATENT DOCUMENTS

EP 575408 B1 * 10/1997

OTHER PUBLICATIONS

Warmuth et al., "Recent Highlights in Hemicarcerand Chemistry," Accounts of Chemical Research, vol. 34, No. 2, pp. 95-105 (2001).
Leontiev et al., "Encapsulation of Gases in the Solid State," Chem. Commun., 2004, pp. 1468-1469 (2004).
Akahane et al., "Fine-Tuned High-Q Photonic-Crystal Nanocavity," Optics Express, vol. 13, No. 4, pp. 1202-1214 (2005).

* cited by examiner

*Primary Examiner*—Rodney Bovernick
*Assistant Examiner*—Omar Rojas

(57) ABSTRACT

A sensor includes traps that are adjacent to a waveguide and capable of holding a contaminant for an interaction with an evanescent field surrounding the waveguide. When held in a trap, a particle of the contaminant, which may be an atom, a molecule, a virus, or a microbe, scatters light from the waveguide, and the scattered light can be measured to detect the presence or concentration of the contaminant. Holding of the particles permits sensing of the contaminant in a gas where movement of the particles might otherwise be too fast to permit measurement of the interaction with the evanescent field. The waveguide, a lighting system for the waveguide, a photosensor, and a communications interface can all be fabricated on a semiconductor die to permit fabrication of an autonomous nanosensor capable of suspension in the air or a gas being sensed.

19 Claims, 1 Drawing Sheet

AUTONOMOUS EVANESCENT OPTICAL NANOSENSOR

CROSS-REFERENCE TO RELATED APPLICATION

This patent document is related to a co-filed U.S. patent application entitled "Passive Evanescent Optical Nanosensor," Ser. No. 11/127,869, which is hereby incorporated by reference in its entirety.

BACKGROUND

Detection of contaminants such as pollutants, toxins, poisons, and biological agents is critically important in many industrial, public, and private environments. Accordingly, a variety of environmental sensors have been developed. These environmental sensors are generally large enough to be handheld or mounted in the areas being monitored. Unfortunately, the size and need for separate mechanical and electrical components make these environmental sensors expensive when compared to the costs of integrated circuits. Sensors that could be manufactured using nanotechnology could potentially reduce sensing costs and permit new sensing capabilities, for example, for environments that are difficult to access or that have insufficient space to accommodate conventional sensors.

Fiber-optic evanescent fluorescence sensors, for example, are a known class of sensors used in biomedical applications. These sensors generally sense or measure the concentrations of target molecules that are known to absorb light having a first wavelength $\lambda$ and to subsequently fluoresce by emitting light having a second wavelength $\lambda'$. Such sensors typically include an optical fiber that is inserted into a liquid containing the target molecules, while light having wavelength $\lambda$ is directed through the optical fiber. The target molecules that are within the evanescent field surrounding the optical fiber can then absorb light of wavelength $\lambda$ from the optical fiber and subsequently fluoresce to emit back into the optical fiber light having wavelength $\lambda'$. A detector coupled to the optical fiber measures the intensity of the light having frequency $\lambda'$, and that measurement indicates the presence or number of target molecules within the evanescent field of the optical fiber.

Current evanescent fluorescence sensors have a number of drawbacks. In particular, such sensors are relatively large and limited to sensing target molecules that have suitable fluorescent properties. Further, evanescent fluorescence sensors are typically limited to sensing target molecules in a liquid because contaminants in a gas at room temperature spend only a short time within the evanescent field, i.e., within a distance of about $\lambda/4$ of the optical fiber, and therefore generally move away from the fiber before fluorescing.

In view of the limitations of current environmental sensors, inexpensive sensors and sensing methods for detecting a variety of contaminant species in a gas or a liquid are needed.

SUMMARY

In accordance with an embodiment of the current invention, a sensor includes: a waveguide; a lighting system coupled to the waveguide; a trap adjacent to the waveguide; a photosensor; and a communications interface. The trap is capable of capturing and holding a target contaminant in an evanescent field of the waveguide, and the photosensor is positioned to detect light from the trap. The communications interface can be connected to the photosensor.

Another embodiment of the invention provides a method for detecting a target contaminant. The method includes capturing a particle of the target contaminant in a trap adjacent to a waveguide. When light is directed down the waveguide, the trap that has captured a particle holds the particle in an evanescent field caused by the light in the waveguide. Light that the target contaminant scatters from the waveguide can be measured.

BRIEF DESCRIPTION OF THE DRAWINGS

Use of the same reference symbols in different figures indicates similar or identical items.

DETAILED DESCRIPTION

In accordance with an aspect of the invention, a sensor can employ traps that capture and hold target contaminants within the evanescent field surrounding a waveguide. The presence or number of particles of the target contaminants in the traps can be detected at anytime after capture by directing light of a desired wavelength through the waveguide and measuring light scattering from the contaminants. Such scattering can occur through many mechanisms including but not limited to linear and nonlinear resonance fluorescence or Raman scattering. The sensors can be made autonomous through integration of the waveguide, the traps, a lighting system, photosensors, and a communications interface into a single device. Further, sensors including the waveguides, the traps, photosensors, and communications interface can be integrated in or on a chip using nanotechnology. Accordingly, millions of inexpensive dust-sized nanosensors (each of which could have hundred or thousands of traps) can be dispersed within a gas and used to detect and map the concentration and/or distribution of the target contaminants.

Reference is now made in detail to specific embodiments, which illustrate the best mode presently contemplated by the inventors for practicing the invention. Alternative embodiments are also briefly described as applicable.

Figure 1:
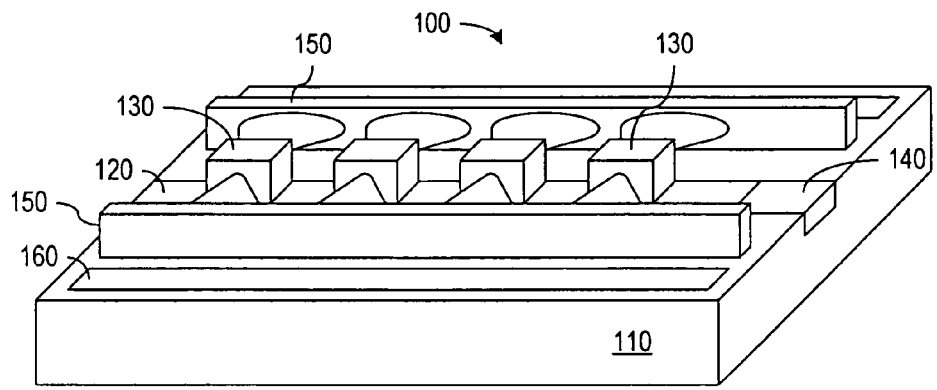
FIG. 1 schematically shows a nanosensor in accordance with an embodiment of the invention including a waveguide, a lighting system, traps, photosensors, and a communications interface.
Figure 2:
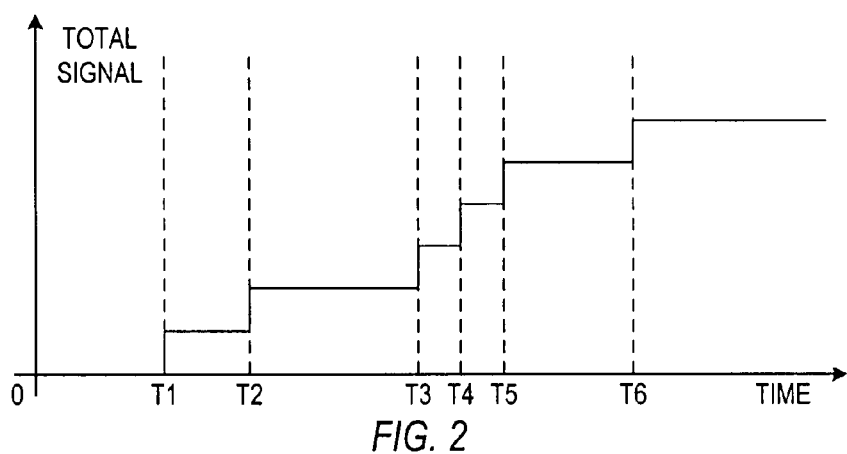
FIG. 2 illustrates the change in an output signal as traps in the sensor of FIG. 1 capture particles of a target contaminant.
Figure 3:
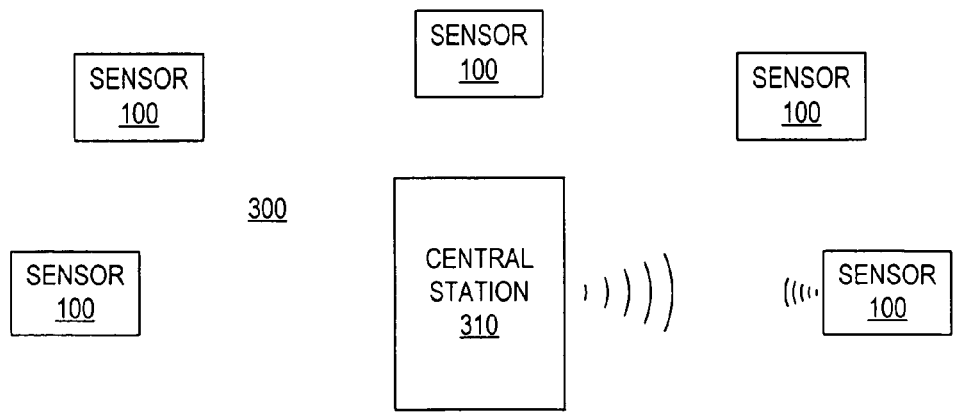
FIG. 3 is a block diagram of a measurement system in accordance with an embodiment of the invention using multiple nanosensors and a central station.

FIG. 1 shows a schematic illustration of a sensor 100 fabricated on a die 110. In an exemplary embodiment of the invention, die 110 is a processed semiconductor chip, e.g., a silicon or GaAs chip, having an area of several square microns. On die 110, sensor 100 includes a waveguide 120, a collection of traps 130, a lighting system 140, photosensors 150, and a communications interface 160.

Waveguide 120 is fabricated in die 110 and has optical characteristics suitable for guiding light or other electromagnetic radiation having a wavelength that interacts with a target contaminant to be measured. In an exemplary embodiment of the invention, waveguide 120 is a channel of dielectric material such as silica, silicon dioxide, or lithium niobate that conventional processing techniques have deposited or grown on die 110. Alternatively, waveguide 120 can be a line defect in a photonic crystal formed in die 110. For a photonic crystal, holes or variations of the refractive index in die 110 can be formed in a pattern such that propagation of light having the desired wavelength is limited to a defect corresponding to waveguide 120. Such defects are generally implemented as a variation in the pattern of the photonic crystal.

Traps 130 are designed to trap a target species or multiple target species of contaminant and are positioned to hold the target contaminant within a volume corresponding to an evanescent field of waveguide 120. Accordingly, sensor 100 can sense contaminants in a gas because traps 130 confine the particles of the contaminant, which may otherwise be fast moving when free in the surrounding gas. Confinement of the particles may either be permanent or at least of sufficient duration for evanescent sensing. The holding of contaminants may be advantageous not only for sensing contaminants in a gas but also for sensing contaminants in liquid, particularly when fluorescence is sensed and the decay time for the contaminant to fluoresce is long. Traps 130 should further be such that traps 130 cause little or no scattering of the light from waveguide 120 when traps 130 are empty. In a typical application of sensor 100, each trap 130 is a molecular trap that is designed to trap the same target molecule. Such molecular traps are well known in the art, and some specific examples of suitable traps are described further below.

Lighting system 140 directs light or other electromagnetic radiation for propagation through waveguide 120. Lighting system 140 is preferably an active light source such as a laser or light emitting diode (LED) that is fabricated in and on die 110 and produces light having a wavelength that causes a target contaminant in the evanescent field of waveguide 120 to fluoresce or otherwise scatter the light. A power source (not shown), which may be, for example, a charged capacitor, an inductor or a receiver tuned to absorb power from an electromagnetic signal, or a photovoltaic cell can be provided on die 110 to power lighting system 140 and other circuit elements of sensor 100. Alternatively, lighting system 140 can be a passive system that directs light from the surrounding ambient into waveguide 120. The contaminants captured in traps 130 can then interact with the evanescent field that the light creates around waveguide 120.

Photosensors 150 can be positioned along waveguide 120 or adjacent to traps 130 to detect light scattered or emitted by the contaminants captured in traps 130. In an exemplary embodiment of the invention, photosensors 150 include two banks of photodiodes that are fabricated in die 110 adjacent to waveguide 120. If desired, the surface of die 110 can be contoured to increase the efficiency with which photosensors 150 collect the light emitted or scattered from traps 130, and baffles and/or optical filters (not shown) may be added to block stray light and to select a range of wavelengths for the light that photosensors 150 measure. Additional sensing circuitry such as a current-to-voltage current converter and/ or an amplifier connected to photosensors 150 can be fabricated in die 110 and used to produce a measurement signal indicating the total intensity of light measured. In the exemplary embodiment of the invention, the measurement signal has an analog voltage or current level proportional to a total current output from the photodiodes in photosensors 150.

Communications interface 160 receives the measurement signal from photosensors 150 and produces an output signal that can be externally received and interpreted. In an exemplary embodiment of the invention, communication circuit 160 includes a radio frequency (RF) transmitter or transceiver that broadcasts an output signal to a remote receiver (not shown). The output signal can simply be an RF signal having an analog intensity that is proportional to the output signal from photosensors 150, so that a receiver can measure the intensity of the RF signal at the frequency used for signaling to determine the amount of contaminant captured in one or more nearby sensors 100. Alternatively, any desired signaling protocol, including but not limited to digital signaling protocols, can convey measurement data from one or more sensors 100 to the central receiver. The central receiver can process the signals from the sensors 100 and estimate the contaminant concentration.

In another alternative embodiment, communications interface 160 implements an optical interface such as described in U.S. patent application Ser. No. 10/684,278, entitled "Photonic Interconnect System," which is hereby incorporated by reference in its entirety.

Sensor 100 as described above uses traps 130 for capturing a target contaminant from a surrounding environment and for binding the captured contaminant within an evanescent field around waveguide 120. In different embodiments of the invention, each captured particle of the target contaminant may be, for example, an atom, a molecule, a virus, or a microbe, and traps 130 generally have a chemistry or structure that is suitable and selected for capture of the target contaminant. Additionally, traps 130 must also firmly attach to the material of waveguide 120, e.g., to silica, or to another material in sensor 100 adjacent to waveguide 120. Particular molecular groups such as chlorine derivatives of silane, are well known to bind strongly to silicon dioxide and other materials. In an exemplary embodiment of the invention, waveguide 120 is formed from silicon dioxide that is uniformly coated with a molecular group of chlorine derivatives of silane, which in turn irreversibly binds traps 130 to waveguide 120.

Some atomic species of environmental contaminants that often need to be monitored include toxins such as arsenic (As) or lead (Pb), fissionable materials such as uranium (U) or plutonium (Pu), and other radioactive materials such as certain isotopes of strontium (Sr). A range of "host-guest" chemistries have been developed for capture of either a specific type of atom or an atom from a specific chemical family such as the alkali metals or the rare earth metals. These host-guest chemistries often discriminate among various atomic or ionic species based on the diameter of the atom or ion. Molecule cages known as carcerands or hemicarcerands, for example, can trap an atom (or a small molecule) and permanently hold the trapped contaminant. In an embodiment of the invention that measures or detects contaminant atoms or small molecules, traps 130 can be implemented as carcerands and hemicarcerands creating a cage of the size required to trap a particle of the target contaminant.

Another type of trap 130 for atomic contaminants uses a chelating compound, such as the well-known bidentate molecule ethylenediamine or the hexadentate molecule EDTA (ethylenediaminetetraacetate), which can form complexes with a target atom. Such chelates can also be bound to waveguide 120 using a chlorosilane chemistry such as mentioned above.

Chemistries that have been developed to complex many of the environmental pathogens or chemical agent molecules can also be used for traps 130 in sensor 100. For example, various bioactive pathogens attack particular molecular structures such as a protein or DNA in cells. For these pathogens, the specific protein or DNA strand may be used as "bait" trapping for the pathogen. Carcerands and other related systems have also been developed for capture of specific molecules (or a specific family of molecules) and could be used as traps 130 that bind a molecular species.

For a larger contaminant such as a virus, e.g. the polio or ebola virus, an antibody for the virus can be bound to waveguide 120 as traps 130 because in many cases the antibody contains a protein that binds specifically to the external coating of the virus particle. Alternatively, traps 130 could include a suitable protein from the antibody or any other type of molecule designed to recognize and bind to a particular virus or include a type of bait that resembles the lipid layer of a cell that attracts the virus.

Finally, sensor 100 could successfully detect microbes using entities such as anthrax spores or other bacterial agents attached to waveguide 120 as traps 130. Alternatively, the cell wall or coatings of microbe contaminants can be recognized or bound using specific proteins or sugars.

In order to achieve a high level of certainty in detection, sensor 100 may to use several different types of traps 130 to recognize and bind the same contaminant on either the same or different waveguides 120. With separate waveguides 120 using different traps 130, a coincidence of separate measurement signals could provide confirmation of trapping of the target contaminant and minimize spurious signals or false positives.

FIG. 2 illustrates the typical behavior of the measurement signal for sensor 100 as a function of time. Ideally, traps 130 are protected from contaminants until a test start time (t=0) or are activated chemically or electromagnetically at the test start time. At a subsequent time T1, a first of the traps 130 captures a target contaminant at which point the scattered light measured by photosensors 150 jumps. At subsequent times T2, T3, T4, T5, and T6, other traps 130 capture additional particles of the target contaminant, causing discrete increases in the scattered light, until all of the traps 130 are filled. The jumps in the measurement signal identify when the target contaminant is detected. Further, the mean rate at which the measurement signal increases indicates the concentration of the target contaminant since higher contaminant concentrations will cause higher rates of capture. Accordingly, with appropriate calibration or analysis, the rate of signal increases or the capture rate can be used to measure the concentration of the target contaminant.

FIG. 3 illustrates a system 300 for using sensors 100 to measure the presence, the concentration, and/or the distribution of a target contaminant. For system 300, a collection of sensors 100, which are nanosensors that are sufficiently small to float in air, are released into an environment to be tested for a target contaminant. Sensors 100 may, for example, be released into a ventilation system in a building. The number of sensors 100 used will generally depend on the expected density of the target contaminant, the size of the environment tested, and how sensitive the environment is to the dust that discarded sensors 100 create when testing is complete. Traps in each sensor 100 distributed into the environment capture particles of the contaminant as sensors 100 move through the environment.

A central station 310 can be moved to any location where sensors 100 are present. In the illustrated embodiment, central station 310 includes a transmitter that transmits a signal to activate one or more sensors 100. The transmitted activation signal may, for example, be a radio or microwave signal that a communications interface 160 receives and converts to power that operates lighting system 140 and other circuit elements in sensors 100. If desired, the activation signal can be directional or limited in range so that only sensors 100 in a particular area are activated.

The activated sensors 100 transmit back measurement signals indicating the number of captured contaminants in the activated sensors 100. Central station 310 can continue monitoring or polling of the measurement signals from sensors 100 over a period of time sufficient to determine rates of increase of the measurement signals and from the rates of increase determine the concentrations of the contaminant in the specific areas containing the activated sensors. Information concerning the presence, the concentration, and the distribution of the target contaminant or contaminants can thus be obtained.

Although the invention has been described with reference to particular embodiments, the description is only an example of the invention's application and should not be taken as a limitation. For example, although the above embodiments often describe use of light and light sources, it should be understood that embodiments of the invention are not limited to use of visible light but more generally can employ other wavelengths of electromagnetic radiation that provide an evanescent field suitable for detection of target contaminants. Various other adaptations and combinations of features of the embodiments disclosed are within the scope of the invention as defined by the following claims.

What is claimed is:

1. A sensor comprising:

a waveguide;

a lighting system coupled to the waveguide;

a trap adjacent to the waveguide, wherein the trap comprises a molecular cage that is capable of capturing and holding a target contaminant in an evanescent field around the waveguide;

a photosensor positioned to detect light from the trap;

a communications interface connected to the photosensor;

wherein the waveguide, the lighting system, the photosensor, and the communications interface are integrated on a semiconductor die.

2. The sensor of claim 1, wherein the waveguide comprises a material selected from the group consisting of silica and lithium niobate.

3. The sensor of claim 1, wherein the lighting system comprises a laser integrated on the semiconductor die.

4. The sensor of claim 1, wherein the trap is attached to the waveguide.

5. The sensor of claim 1, wherein the communications interface comprises the RF transceiver.

6. The sensor of claim 1, further comprising a plurality of traps that are adjacent to the waveguide and capable of capturing and holding the target contaminant in the evanescent field around the waveguide.

7. The sensor of claim 6, wherein the communications interface broadcasts an output signal indicating a number of the traps that are holding the target contaminant.

8. The sensor of claim 1, wherein the sensor operates to sense the target contaminant in a gas.

9. The sensor of claim 1, wherein the sensor has a size such that the sensor can float in air while sensing for the target contaminant in the air.

10. The sensor of claim 1, wherein the molecular cage is selected from a group consisting of a carcerand and a hemicarcerand.

11. A method for detecting a target contaminant, comprising:

directing light through a waveguide using a lighting system;

capturing the target contaminant in a trap adjacent to the waveguide, wherein the trap comprises a molecular cage that holds the target contaminant in an evanescent field of the light in the waveguide;

measuring light that the target contaminant in the trap scatters from the waveguide using a photosensor;

wherein the waveguide, the lighting system, and the photosensor are integrated on a semiconductor die.

12. The method of claim 11, further comprising providing an integrated nanosensor that includes:
the waveguide and
a plurality of traps.

13. The method of claim 12, further comprising transmitting an output signal from the nanosensor, wherein the output signal indicates a total intensity of light scattered from the waveguide, at the traps.

14. The method of claim 13, further comprising determining a concentration of the target contaminant from a rate of change in the total intensity of the light scattered at the traps.

15. The method of claim 13, wherein the light scattered at the traps has a wavelength that is the same as a wavelength of the light directed through the waveguide.

16. The method of claim 13, wherein the light scattered at the traps has a wavelength that differs from a wavelength of light directed through the waveguide.

17. The method of claim 11, wherein capturing the target contaminant comprises exposing the trap to a gas containing the target contaminant, wherein the trap captures the target contaminant from the gas.

18. The method of claim 12, wherein capturing the target contaminant comprises permitting the nanosensor to float in air, wherein the traps capture the target contaminant from the air.

19. The method of claim 12, wherein the molecular cage is selected from a group consisting of a carcerand and a hemicarcerand.

* * * * *

UNITED STATES PATENT AND TRADEMARK OFFICE
CERTIFICATE OF CORRECTION

| | | |
|---|---|---|
| PATENT NO. | : 7,233,711 B1 | Page 1 of 1 |
| APPLICATION NO. | : 11/127542 | |
| DATED | : June 19, 2007 | |
| INVENTOR(S) | : Raymond G. Beausoleil et al. | |

It is certified that error appears in the above-identified patent and that said Letters Patent is hereby corrected as shown below:

On the face page, in field (73), in "Assignee", in column 1, line 1, delete "Hewlett Packard" and insert -- Hewlett-Packard --, therefor.

In column 6, line 42, in Claim 5, delete "the" and insert -- an --, therefor.

Signed and Sealed this

Fourteenth Day of July, 2009

JOHN DOLL
*Acting Director of the United States Patent and Trademark Office*